United States Patent
Hakki et al.

(10) Patent No.: US 10,500,394 B1
(45) Date of Patent: Dec. 10, 2019

(54) PACEMAKER SYSTEM EQUIPPED WITH A FLEXIBLE INTERCOSTAL GENERATOR

(71) Applicants: A-Hamid Hakki, Dunedin, FL (US); A-Hadi Hakki, Largo, FL (US)

(72) Inventors: A-Hamid Hakki, Dunedin, FL (US); A-Hadi Hakki, Largo, FL (US)

(*) Notice: Subject to any disclaimer, the term of this patent is extended or adjusted under 35 U.S.C. 154(b) by 0 days.

(21) Appl. No.: 15/691,924

(22) Filed: Aug. 31, 2017

Related U.S. Application Data

(63) Continuation-in-part of application No. 15/042,301, filed on Feb. 12, 2016, now Pat. No. 9,775,991, which
(Continued)

(51) Int. Cl.
*A61N 1/36* (2006.01)
*A61N 1/05* (2006.01)
(Continued)

(52) U.S. Cl.
CPC ............ *A61N 1/057* (2013.01); *A61N 1/362* (2013.01); *A61N 7/00* (2013.01)

(58) Field of Classification Search
CPC ....... A61N 1/057; A61N 1/362; A61N 1/3756
See application file for complete search history.

(56) References Cited

U.S. PATENT DOCUMENTS

| 3,454,012 A | 7/1969 | Raddi |
| 3,824,129 A | 7/1974 | Fagan, Jr. |

(Continued)

FOREIGN PATENT DOCUMENTS

| WO | 1997013941 A1 | 4/1997 |
| WO | 1998032485 A1 | 7/1998 |

(Continued)

OTHER PUBLICATIONS

K.L. Lee, et al., First Human Demonstration of Cardiac Stimulation with Transcutaneous Ultrasound Energy Delivery: Implications for Wireless Pacing with Implantable Devices. J Am Coll Cardiol. 2007;50:877-83.

(Continued)

*Primary Examiner* — Alyssa M Alter
(74) *Attorney, Agent, or Firm* — Rosenberg, Klein & Lee

(57) ABSTRACT

A pacemaker system is configured to sense electrical and mechanical activity of the heart tissue within a mammalian body and to generate a corresponding signal responsive to the sensed cardiac activity. The system includes a flexible electrical generator that contains EKG (ECG) electrodes for measuring electrical activity and ECHO piezoelectric electrodes for measuring mechanical activity of the heart and Doppler blood flow. The generator is embedded in a flexible shield, and is contoured to conform to the anatomy of the intercostal space to be embedded between the ribs of a patient and in the position overlying the heart. The system provides for pacing as well as defibrillation, responsive to the readings of the heart activities. A microprocessor analyzes a cardiac situation, based on the sensor's readings, produces a diagnosis, and generates control signals, such as "pacing pulse" in a life-threatening situation, or "observe" in a non life-threatening situation.

20 Claims, 4 Drawing Sheets

Related U.S. Application Data is a continuation-in-part of application No. 13/649,792, filed on Oct. 11, 2012, now Pat. No. 9,289,593.

(60) Provisional application No. 61/545,913, filed on Oct. 11, 2011.

(51) Int. Cl.
*A61N 7/00* (2006.01)
*A61N 1/362* (2006.01)

(56) References Cited

U.S. PATENT DOCUMENTS

| | | |
|---|---|---|
| 3,867,950 A | 2/1975 | Fischell |
| 4,014,346 A | 3/1977 | Brownlee et al. |
| 4,332,256 A | 6/1982 | Brownle et al. |
| 5,224,491 A | 7/1993 | Mehra |
| 5,282,845 A | 2/1994 | Bush et al. |
| 5,350,413 A | 9/1994 | Miller |
| 5,383,922 A | 1/1995 | Zipes et al. |
| 5,411,537 A | 5/1995 | Munshi et al. |
| 5,690,693 A | 11/1997 | Wang et al. |
| 5,702,431 A | 12/1997 | Wang et al. |
| 5,749,833 A | 5/1998 | Hakki et al. |
| 5,814,089 A | 9/1998 | Stokes et al. |
| 5,902,331 A | 5/1999 | Bonner et al. |
| 6,148,237 A | 11/2000 | Das |
| 6,161,029 A | 12/2000 | Spreigl et al. |
| 6,185,464 B1 | 2/2001 | Bonner et al. |
| 6,219,581 B1 | 4/2001 | Schaldach et al. |
| 6,256,543 B1 | 7/2001 | Spence |
| 6,345,198 B1 | 2/2002 | Mouchawar et al. |
| 6,370,427 B1 | 4/2002 | Alt et al. |
| 6,400,992 B1 | 6/2002 | Borgersen et al. |
| 6,434,430 B2 | 8/2002 | Borgersen et al. |
| 6,445,953 B1 | 9/2002 | Bulkes et al. |
| 6,505,081 B1 | 1/2003 | Das |
| 6,522,915 B1 | 2/2003 | Ceballos et al. |
| 6,529,777 B1 | 3/2003 | Holmstrom et al. |
| 6,544,270 B1 | 4/2003 | Zhang |
| 6,574,512 B1 | 6/2003 | Zhang et al. |
| 6,584,352 B2 | 6/2003 | Combs et al. |
| 6,654,638 B1 * | 11/2003 | Sweeney .................. A61N 1/056 607/2 |
| 6,654,644 B2 | 11/2003 | Sanchez-Zambrano |
| 6,658,289 B2 | 12/2003 | Helland |
| 6,671,562 B2 | 12/2003 | Osypka et al. |
| 6,675,045 B2 | 1/2004 | Mass et al. |
| 6,721,600 B2 | 4/2004 | Jorgenson et al. |
| 6,772,015 B2 | 8/2004 | Dahl et al. |
| 6,788,972 B2 | 9/2004 | Prutchi et al. |
| 6,795,732 B2 | 9/2004 | Stadler et al. |
| 6,856,835 B2 | 2/2005 | Bardy et al. |
| 6,868,291 B1 | 3/2005 | Bonner et al. |
| 6,871,101 B2 | 3/2005 | Zhang et al. |
| 6,885,889 B2 | 4/2005 | Chinchoy |
| 6,936,040 B2 | 8/2005 | Kramm et al. |
| 6,968,236 B2 | 11/2005 | Hagele |
| 6,973,351 B2 | 12/2005 | Morgan |
| 6,980,850 B1 | 12/2005 | Kroll et al. |
| 6,985,777 B2 | 1/2006 | Tsuboi et al. |
| 6,988,001 B2 | 1/2006 | Greatbatch et al. |
| 6,993,379 B1 | 1/2006 | Kroll et al. |
| 7,031,774 B1 | 4/2006 | Doan et al. |
| 7,047,086 B2 | 5/2006 | Taskiran et al. |
| 7,092,766 B1 | 8/2006 | Salys et al. |
| 7,982,370 B2 | 7/2011 | Wang et al. |
| 8,923,963 B2 | 12/2014 | Bonner et al. |
| 9,072,914 B2 | 7/2015 | Greenhut et al. |
| 9,216,280 B1 | 12/2015 | Hakki et al. |
| 9,289,593 B1 | 3/2016 | Hakki et al. |
| 9,406,826 B2 | 8/2016 | Plug et al. |
| 9,673,481 B2 | 6/2017 | Sabi et al. |
| 2002/0035381 A1 | 3/2002 | Bardy et al. |
| 2002/0193836 A1 | 12/2002 | Schmidt |
| 2003/0092977 A1 | 5/2003 | Sahatjian |
| 2004/0167416 A1 * | 8/2004 | Lee ..................... A61B 5/0031 600/513 |
| 2004/0176672 A1 | 9/2004 | Silver et al. |
| 2008/0255642 A1 | 10/2008 | Zarins et al. |
| 2016/0067479 A1 * | 3/2016 | Marcovecchio ..... A61N 1/0592 606/129 |

FOREIGN PATENT DOCUMENTS

| | | |
|---|---|---|
| WO | 0004950 A2 | 2/2000 |
| WO | 2002087501 A2 | 11/2002 |
| WO | 2004045675 A2 | 6/2004 |
| WO | 2006083617 A2 | 8/2006 |

OTHER PUBLICATIONS

D. Reynolds, et al., A Leadless Intracardiac Transcatheter Pacing System, The New England Journal of Medicine, Nov. 10, 2015.

M. Schoenfeld, Contemporary Pacemaker and Defibrillator Device Therapy: Challenges Confronting the General Cardiologist. J. Am. Heart Association. 2007; 115:638-53.

* cited by examiner

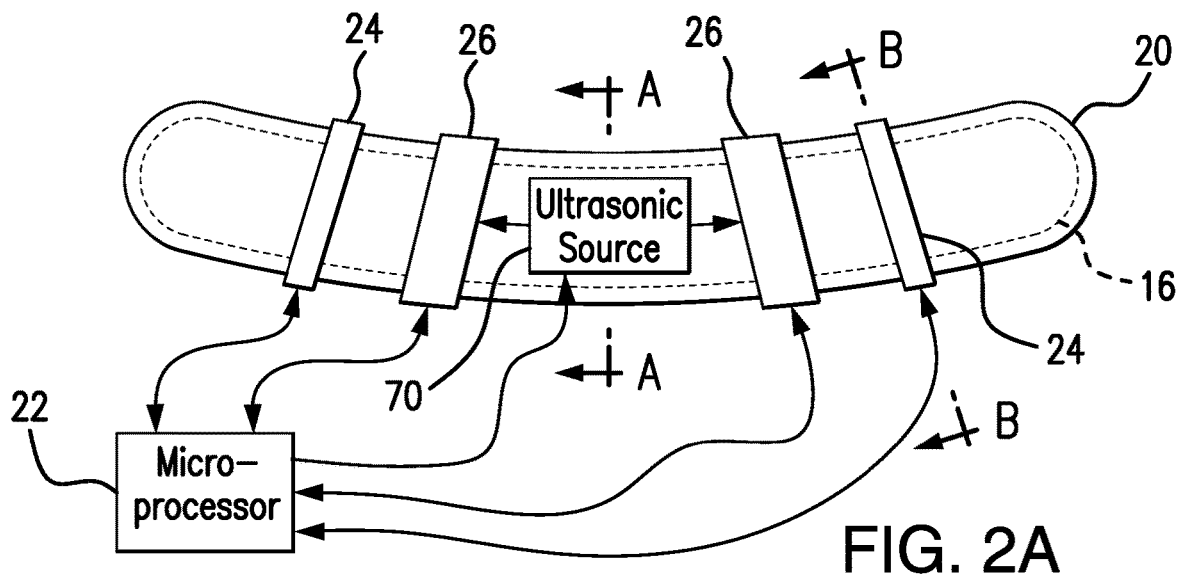
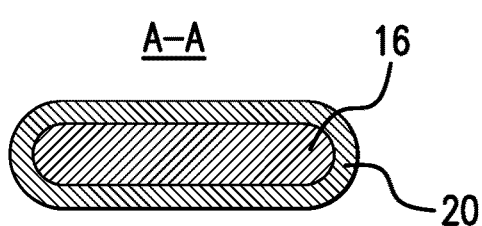 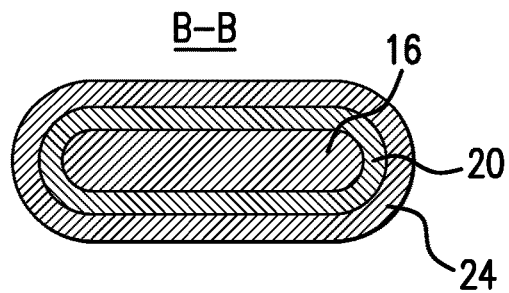
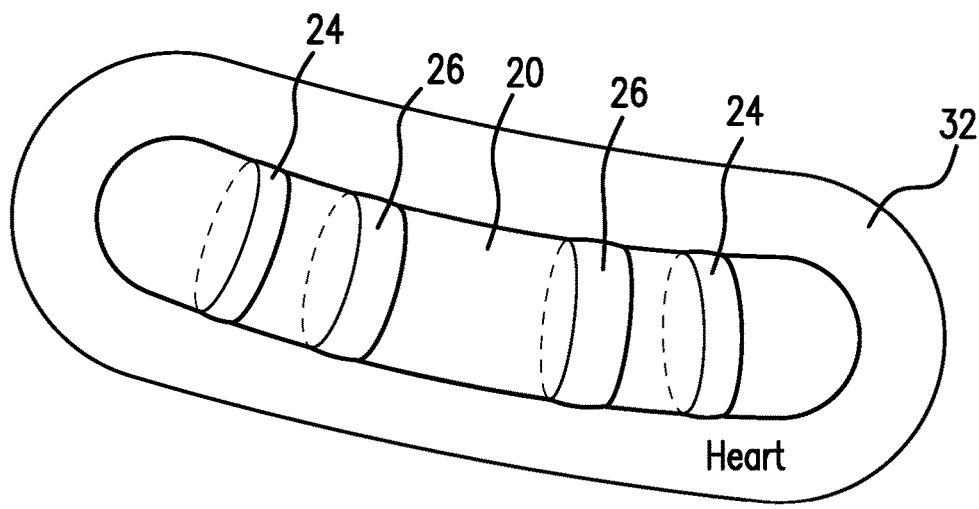
FIG. 2A
FIG. 2B
FIG. 2C
FIG. 2D

PACEMAKER SYSTEM EQUIPPED WITH A FLEXIBLE INTERCOSTAL GENERATOR

REFERENCE TO RELATED APPLICATIONS

This application is a Continuation-in-Part of patent application Ser. No. 15/042,301 filed on 12 Feb. 2016 which is a Continuation-in-Part of patent application Ser. No. 13/649,792 filed on 11 Oct. 2012, now U.S. Pat. No. 9,289,593 and issued on 22 Mar. 2016, which was based on Provisional Patent Application Ser. No. 61/545,913 filed on 11 Oct. 2011.

INCORPORATION BY REFERENCE patent application Ser. No. 15/042,301; patent application Ser. No. 13/649,792 and Provisional Patent Application Ser. No. 61/545,913 are hereby incorporated by reference.

FIELD OF THE INVENTION

The present invention relates to the field of cardiology, and in particular, to implantable pacemaker systems.

More in particular, the present invention is directed to treatment of symptomatic bradycardia using a subcutaneous generator surgically implanted in the intercostal space in proximity to the heart of a patient to provide electrical cardiac pacing which does not require trans-venous leads.

Still further, the present invention relates to a leadless pacemaker system providing pacing of cardiac tissues responsive to readings of sensors employed in the system that detects electrical, Doppler cardiac/vascular blood flow, and mechanical cardiac activity.

In addition, the present invention relates to a pacemaker leadless system for pacing cardiac tissues using a flexible generator implanted beneath the skin in the intercostal space in order to avoid interference with the chest wall and ribs motion.

Furthermore, the present invention relates to a pacemaker leadless system for pacing the cardiac tissue by means of a miniature generator implant that is rechargeable from a power source external to the chest wall through inductive charging to wirelessly transfer energy from the power source to replete the generator's battery.

In addition, the subject invention relates to a system for sensing myocardial electrical impulses and for providing low or high voltage pacing and defibrillation responsive to the sensed cardiac activity.

The subject invention is further directed to a pacemaker system configured for stimulation of cardiac tissues using electric, ultrasound, and/or magnetic stimulation.

The subject inventive concept is also directed to a pacemaker system adapted for simultaneous pacing of right and left cardiac chambers facilitated by a wireless generator which provides a homogeneous electric field for defibrillation needed for treating heart failure.

Moreover, the subject invention is directed to a pacemaker system which operates based on an algorithm for heart stimulation and which uses mechanical sensors of cardiac motion and Doppler blood flow (such as operating with ultrasound/Doppler piezoelectric crystals), as well as electrical sensors, in order to detect and verify the presence (or absence) of life-threatening arrhythmias, thus minimizing the risk of inappropriate cardiac shocks.

BACKGROUND OF THE INVENTION

Conventional cardiac pacemakers and defibrillators are generally equipped with a generator for electrical stimulation that is implanted in a patient's body distally from the heart for cardiac pacing and defibrillation.

Conventional cardiac pacemakers may typically be designed as a single chamber or a dual chamber device. The single chamber device is capable of sensing and pacing in one cardiac chamber, either the atrium or the ventricle. Dual chamber devices have the capability of sensing and pacing in both (atrium and ventricle) cardiac chambers.

In addition to the right atrium pacing and the ventricle pacing, the left ventricle (by way of the cardiac veins or bi-ventricular pacing) provides a physiologic and synchronous cardiac contraction which would improve cardiac function.

Modes of pacing operations may be identified through letter sequences which include the following identifications: VDD, DVI, VVI, and DDD. The first letter of the mode identification indicates the cardiac chamber being paced. The second letter indicates the cardiac chamber being sensed. The third letter indicates the responses being inhibited or triggered. A fourth letter "R" may be added to the mode identifications which denotes a rate responsive pacing to match patient's activities.

The conventional cardiac pacemakers are equipped with elongated flexible pacemaker leads (cardiac leads) which are typically connected to the generator. The cardiac leads are conventionally configured with tubular electrically insulated sleeve structures that are inserted into the body through an incision overlying the veins and leading to the heart chambers where a distal end of each lead is lodged. In such cases, the distal end of the cardiac lead is connected to a tubular tip electrode which has an increased diameter forming an annular shoulder against which the distal end of the tubular sleeve abuts.

Conventionally, two types of cardiac leads are used in the pacemaker systems, i.e., the uni-polar leads and the bipolar leads. The uni-polar cardiac lead operates with a single conductor coil, and typically includes a cathode (or negative pole) at the distal tip, and an anode (or positive pole) defined by the housing of the stimulator. Electric current returns to the anode via the body tissue as a current path.

The bipolar cardiac lead has two conductor coils, the distal tip forming the cathode, and an annular (or ring) electrode located a few millimeters proximal to the distal tip. High voltage defibrillation is delivered by one or two shocking coils that are inserted intravenously.

Pacemaker leads (referred to herein intermittently also as cardiac leads) are generally adapted for placement in the ventricle and atrium. In order to provide permanent pacing and to avoid the pacemaker lead dislodgement, various techniques have been used for anchoring the pacemaker leads to the endocardium (which is the inner lining of the heart chambers). Pacing the right ventricular outflow is desirable due to antegrade conduction, compared to retrograde conduction that is inherent with apical pacing.

However, right ventricular outflow pacing may not be feasible using conventional transvenous electrodes due to the difficulty of securing a stable position and the high risk of dislodgment. Conventional right ventricular apical pacing alters the normal synchronization of different heart chambers, and may adversely influence ventricular function, leading to heart failure.

In addition, right ventricular leads in conventional pacemakers, when implanted, disadvantageously cross the tricuspid valve which is located on the right dorsal side of the heart between the right atrium and the right ventricle. Such leads may cause unwanted tricuspid regurgitation by interfering with tricuspid valve closing during heart contraction which may interfere with the right ventricular function.

Bi-ventricular pacing (or resynchronization) requires the placement of electrodes within the venous system of the heart. However, other than lodging the tip of the lead into the distal coronary vein, there has been found no safe anchoring mechanism to maintain the lead from dislodging. Screw-in anchors may be applied to the myocardium, but cannot be utilized in vascular structures due to the risk of endothelial damage and hemorrhage.

Additionally, the optimum lodging site may not be the ideal pacing location for effective myocardial stimulation.

PRIOR ART

Cardiac pacing systems have been used for treatment of symptomatic bradycardia through cardiac pacing using surgically inserted subcutaneous generators in conjunction with one or more transvenous leads that provide electrical pacing to the cardiac conduction system. Conventional pacemaker generators sense electrical cardiac activity by electrodes embedded in the endocardium or vascular structures of the heart. Without the electrodes, generators are unable to detect electrical cardiac activity.

However, complications arise in a large percentage of patients which are directly related to the use of the electrical generator or the transvenous lead wire system. These problems are usually associated with infection, pocket hematoma, pneumothorax, lead fracture, dislodgement, and vascular access limitations.

Single chamber ventricular systems are generally limited to patients with atrial fibrillation and slow ventricular response which do not require frequent pacing. Frequent ventricular apical pacing has been shown to be deleterious to cardiac function. There are numerous conditions which would preclude the implantation of a transvenous pacemaker system, such as compromised venous access, the need to preserve veins for hemodialysis, thrombosis, a patient's history of infection, or the need for an indwelling venous catheter.

Rarely used nowadays are "fixed rate" pacemakers that activate the heart, regardless of the underlying heart rhythm, while most pacemaker are "demand inhibited" that stimulate the heart only when the intrinsic heart rhythm falls below a certain level, designated as bradycardia or slow heart rhythm.

Conventional cardiac pacemakers comprise electrodes attached to a pulse generator (that contains microelectronics to control pacemaker functions), a battery source for supplying electricity to the microelectronics package, and other peripheral components.

The electrodes carrying the electric impulse are typically secured to the lining of the heart chambers. The pacemaker microelectronics contain circuits and antennas that communicate percutaneously (noninvasively) with external programming transceivers commonly used to interrogate stored pacemaker data and reprogram pacemaker function as deemed appropriate.

Extravascular pacemakers have been developed to circumvent the problems of pacemakers with vascular access. The extravascular implantable cardioverter defibrillator (EV-ICD) manufactured by Medtronic was designed to deliver an electric shock to prevent sudden death, as well as pacing the heart to treat abnormal rapid heart beating. As required by the EV-ICD design, the defibrillation leads are delivered via an introducer under the rib cage. Unfortunately, the device is relatively bulky (having the volume of about 33 ml). The features of the Extravascular-ICD (EV-ICD) system are presented in Table 1.

TABLE 1

Features of Extravascular Pacing systems

| Features | EV-ICD* | Subject Generator |
|---|---|---|
| Leadless | No | Yes |
| Extravascular | Yes | Yes |
| Energy for effective defibrillation | Lower | Higher |
| Ideal for intercostal location | No | Yes |
| Device volume (ml) | 33 | 7 |
| Battery longevity (years) | 10 | Unknown |
| Ease of recharging (external source) | No | Yes |
| Proximal to external electric source | No | Yes |
| Coupling device coil | No | Yes |
| Flexible design | No | Yes |
| Percutaneous insertion | No | Yes |
| May require sternotomy | Yes | No |
| Electrical defibrillation algorithm | Yes | Yes |
| Mechanical defibrillation algorithm | No | Yes |
| Doppler flow defibrillation algorithm | No | Yes |
| Detect electromechanical dissociation | No | Yes |
| Ultrasound sensing and pacing | No | Yes |
| Electrical stimulation | Yes | Yes |
| Low profile thin elongated design | No | Yes |
| Ease to detect device infection | No | Yes |
| Easy device extraction** | No | Yes |

*Extravascular-ICD system by Medtronic
**Needed for depleted battery, or infected device Darius Sholevar, et al. demonstrated the feasibility of cardiac pacing from the substernal space (Substernal Pacing Acute Clinical Evaluation, or SPACE). In operation, the energy amount used for effective defibrillation is about half of that used by subcutaneous ICDs, and is comparable to the energy consumption for conventional transvenous ICDs.

Recharging of implanted devices (such as artificial heart and cardio pacemakers) remains a serious problem in the field of cardiology. Wireless recharging is preferably used for battery recharging. For a wireless cardio implant system, it is desirable that generators detect and induce electrical and mechanical action. Such conventional generators are generally disk-shaped and may not be suitable for operability in close proximity to cardiac structures.

Inductive charging has been used for rechargeable tooth brushes since the 1990s, and more recently, for mobile phones and watches. Transcutaneous Energy Transfer systems have been used to recharge artificial hearts and cardiac pacemakers.

Rechargeable cardiac pacemakers using nickel-cadmium and zinc-mercuric systems are disclosed in U.S. Pat. Nos. 3,454,012; 3,824,129; 3,867,950; and 4,014,346. These pacemakers contain a charging circuit energized by electromagnetic induction from an external source. The "electromagnetic induction" generates a current in the pacemaker's charging circuit that is converted to a direct current voltage to charge the battery.

The systems described in the above-referenced U.S. Patents are prone to problems due to frequent charging. Specifically, these pacemakers may suffer from memory effects that can lead to reduction of the battery capacity exponentially after each recharge, as well as poor specific energy density, low cell voltage and liberation of hydrogen gas. In order to obviate the inherent limitations of the zinc-mercuric oxide and nickel-cadmium battery cells, lithium batteries were introduced (described, for example, in U.S. Pat. No. 5,411,537).

Ideally, electrical energy is transmitted through the skin of a patient between a transcutaneous energy transfer device and an implanted medical device. For example, U.S. Pat. No. 5,350,413 teaches a transcutaneous energy transfer device using an external primary coil located outside the skin, and a secondary coil implanted under the skin. The primary coil induces current in the secondary coils, thus forming a transformer.

Wang, et al. (U.S. Pat. Nos. 5,690,693 and 5,702,431) described an improved transcutaneous energy transmission to charge rechargeable batteries in implanted medical devices. The system comprises a primary coil resonant circuit and a secondary coil attached to the medical device. A sinusoidal waveform current is generated by operating two solid state switches (turned OFF and ON) and is applied to the primary coil and a capacitor to induce a current that may be used to recharge the battery in the medical device.

Wang, et al. addressed an alignment mechanism located in the recharging device, without the need for extra components in the implanted device in addition to the components needed for charging. Wang, et al.'s energy transmission system minimizes the size of the receiving coil and permits the coil to be located inside the housing of the implantable device.

Brownlee, et al., (U.S. Pat. No. 4,332,256), developed a system for telemetering and testing the functions of an implanted pacemaker from a remote location.

Wang, et al. (U.S. Pat. No. 7,982,370) disclosed a miniature electrical generator with piezoelectric fine wire extending along the surface of an elongated substrate. The piezoelectric nanowires extend radially to generate electricity.

Plug, et al. (U.S. Pat. No. 9,406,826) developed a flexible electrical generator consisting of at least one photovoltaic device attached to a flexible support made of high strength polymeric semi-crystalline fabric.

Sabi, et al. (U.S. Pat. No. 9,673,481) introduced a thin film solid state lithium battery with an electric insulating substrate.

Using "wireless power transfer", the EM energy may be transmitted from an outside source to the generator embedded beneath the skin. Such feature is desirable in order to minimize the size of conventional generators which are usually bulky and are not ideally designed for implantation into a patient's body.

It would be highly desirable to provide a miniature generator well-suited for implantation into the patient's body and prolonged battery life.

In the pacemaker's operation, an appropriate shock should be produced and delivered to the heart. The appropriate shock is defined as a shock delivered for a life threatening arrhythmia, such as ventricular tachycardia or ventricular fibrillation.

Among patients with heart failure in whom an ICD is implanted for primary prevention of sudden cardiac death, about ⅓ will experience an inappropriate shock over a period of 1-3 years, i.e. shock for a non-life-threatening arrhythmia, with devastating psychologic impact. The inappropriate shock may be related to supraventricular tachycardia, QRS and T wave double sensing, electromagnetic interference, diaphragmatic sensing, lead fracture, insulation break, or lead dislodgment.

The inappropriate electric shocks constitute a major problem in arrhythmia detection algorithms in implantable cardioverter defibrillators.

Rhythm discrimination is conventionally performed which is based on analysis of the electrocardiographic waveforms. Theuns, et al. (Europace, 2001; 3:181-186) proposed the addition of atrial sensing to ventricular sensing in order to improve the discrimination methodology between ventricular and supraventricular arrhythmias.

All conventional algorithms for pacing/shocking use the routine of sensing cardiac electric activities to make decisions for delivery of shocks to the heart.

However, the conventional systems do not take into account the presence or absence of echocardiographic left ventricular wall motion or function, or Doppler blood flow, which may lead to incorrect results of the analysis, and, in extreme cases, is dangerous to the patient's wellbeing.

U.S. Pat. No. 6,654,683, describes an ultrasonically activated implantable cardiac electrode system which is equipped with piezoelectric elements for converting mechanical energy into electrical energy sufficient to cause pacing of the cardiac tissue. Mechanical energy may originate from an external source low frequency ultrasound transmitter. The electrical energy produced by the piezoelectric element delivers pacing level electrical energy between the system's anode/cathode. Active fixation elements using tines, hooks, and barbs are provided.

However, the '683 patent does not address the use of an external ultrasound generator or application of the ultrasound energy to the heart directly from a source implanted in the intercostal space to induce electrical stimulation of the heart tissue which does not require piezoelectric elements.

The intercostal space is the space defined between the ribs of the chest overlying the heart. The intercostal region would be an ideal location for implanting a pacemaker because it can provide an interference free operation for the pacemaker system. However, none of the conventional pacemaker systems have been adapted for positioning in the intercostal region of a mammalian body. A compact electrical generator operating with double-action electrodes attached to the generator would be desirable if configured to conform to the intercostal space for being embedded therein in close proximity to cardiac structures for sensing heart activity and Doppler blood flow and providing transfer of electrical/ultrasound/Doppler/infrared and/or magnetic stimulation signals to the heart responsive to the sensed cardiac situation without interference from lung tissue or ribs.

In addition, existing pacemaker systems do not operate in accordance with an algorithm for determining the timing and sequence of stimulation of cardiac tissues based on additional sensing of mechanical cardiac motion and blood flow sensed by ultrasound (Doppler) echocardiography to reduce the risk of inappropriate shocks.

Conventional pacemaker generators permit sensing electrical cardiac activity by use of electrodes imbedded into the endocardium or vascular structures of the heart. Without electrodes, generators in conventional pacemakers are unable to detect electrical cardiac action. It would be highly desirable to provide a pacemaker which does not require insert of electrodes into the endocardium or vascular structures of the heart.

The conventional pacemakers generally use disc shaped generators, or capsule shaped nano devices implantable in the patient's body. The disc shaped generators are not suitable for use in close proximity to cardiac structures, unless surgically implanted during heart surgery. None of the conventional pacemakers is equipped with a generator that would be flexible, curved along its longitudinal axis, and having a low (near-flat) profile to accommodate the contour and dimensions of the intercostal space for being inserted percutaneously, and which would be easily rechargeable.

A novel generator having a curvilinear elongated shape would be desirable to conform to the intercostal space (the space between the ribs of the chest overlying the heart) which would permit sufficient proximity to cardiac structures for effective leadless transfer of electrical, ultrasound, Doppler, infrared and magnetic stimulation signals between the generator and the heart of the patient.

SUMMARY OF THE INVENTION

It is, therefore, an object of the present invention to provide a leadless pacemaker system equipped with a flexible generator implantable in dynamically changing sites in the patient's body.

Another object of the current invention is to provide a pacemaker system equipped with a flexible generator implant having a low profile (near-flat) elongated structure conforming with the anatomy of the intercostal space and suitable for implanting therein and providing a stimulation of the heart tissues directly from a power source implanted in the intercostal region in close proximity to the heart.

Furthermore, it is an object of the present invention to provide a pacemaker system equipped with a miniature generator (occupying a small fraction of the size of conventional generators) which is adapted for a wireless recharging of the generator's battery from an external source.

It is another object of the present invention to provide a pacemaker system operating in accordance with an algorithm which is configured to take into account (in addition to the electrical activity of the heart) the presence or absence of echocardiographic ventricular wall motion and function, as well as the Doppler blood flow, which ensures correct readings and analysis of the cardiac state and which results in preventing generation of inappropriate electrical signals that result in shocks/pulses, thus increasing a chance for the patient's well being.

Another object of the present invention is to provide a pacemaker system which uses echocardiographic and Doppler sensing and blood flow in the analysis of heart function to detect life threatening heart rhythm.

It is an additional object of the present invention to provide an implantable pacemaker system which is configured with the abilities to sense, pace, and shock various cardiac tissues supported by a generator that is equipped with electric and ultrasonic elements capable of sensing electrical and mechanical activity of the heart, as well as Doppler blood flow signals from the heart of a patient for correct diagnosis of the cardiac situation.

It is a further object of the present invention to provide a pacemaker system having a generator embedded into the patient's body in close proximity to the heart and equipped with double-action electrodes capable of leadless sensing the electrical and mechanical activity of the heart, and delivery of electric and ultrasonic impulses directly to the heart when triggered by a generator's microprocessor which is configured for making a diagnosis based on the sensors' readings.

It is also an object of the present invention to provide a pacemaker system equipped with a miniature generator implant which houses echo sensors which include piezoelectric crystals which serve to sense mechanical function of, and Doppler blood flow from the heart, where an ultrasonic power source is embedded with the generator to deliver high ultrasonic energy directly to the heart to stimulate the heart when triggered by the generator's microprocessor.

It is still an object of the present invention to provide a wireless cardio implant system equipped with a flexible, curved, elongated and low-profile (near-flat) easily rechargeable generator adapted for percutaneous implantation into the intercostal space of the chest chamber to be in close proximity to cardiac structures for leadless pacing of the heart using the electrical/ultrasound/Doppler/infrared and magnetic stimulation free from the interference from lung tissues or ribs.

Also, it is an object of the present invention to provide a pacemaker system operating in accordance with an algorithm for triggering defibrillation action based on mechanical heart activity and Doppler blood flow in addition to the heart's electrical activity.

In one aspect, the present invention is directed to a system for generating and sensing electrical energy transmitted to and from tissue within a mammalian body. The present system, for example, a cardiac pacemaker system, includes:

a flexible tube-like elongated shaft (also referred to herein as a shield) configured for implanting within the intercostal space between the ribs of the chest chamber of a patient. The generator's flexible shaft (shield) has an elongated low-profile curved body which is adapted for insertion within a patient's intercostal space percutaneously or surgically. The flexible shaft of the subject generator is formed of an electrically conductive EMI/RFI shielding composition, and is contoured to assume a shape and dimensions of the intercostal space in the chest chamber.

The subject system further includes:

a flexible electrical generator capable of sensing and producing electrical and ultrasonic energy and embedded within the flexible shaft; and a number of double-action electrodes coupled to the generator and or the generator's shaft. When the generator is implanted in the intercostal region, the electrodes are disposed in a close proximity to and in facing position with the heart of a patient.

The generator's electrodes operate based on different physical principles and are configured for a double-action operation, i.e., to both sense the heart activity (electrical and mechanical activity of the heart, as well as blood flow from the heart) and to deliver stimulation pulses to the heart when needed. The generator's electrodes may include at least one piezoelectric crystal embedded within (or positioned circumferentially of) the generator or the generator's shield and disposed in a facing position with the heart of the patient. The piezoelectric crystals are configured as echo sensors to perform measurements of mechanical heart function by continuous and pulsed Doppler echocardiographic signals for diagnostic purposes.

In addition, the generator is equipped with an internal ultrasonic source which makes the generator capable of delivering high energy ultrasonic bursts directly to the heart tissue for therapeutic purposes when commanded by the generator's microprocessor.

The electrical generator, as one of its functions, is configured to detect the electrical activity of a patient's heart. For this purpose, the generator's electrodes include at least one electrically conductive electrode attached to the generator or the generator's shaft for sensing leadlessly the heart's electrical activity. The subject generator is also configured to provide high voltage pacing and low voltage pacing via the electrically conductive electrodes.

The echo sensors are capable of operating with pulsed, as well as continuous, Doppler ultrasound signals to detect mechanical heart function or lack thereof. The generator is further equipped with an embedded ultrasound and Doppler source in proximity to the echo electrode to support the direct pacing operation.

The subject generator produces electric and ultrasonic pacing (or shock) pulse responsive to the combined readings corresponding to electrical, as well as mechanical, activities of the heart tissues, and the blood flow readings, acquired to diagnose a life threatening heart rhythm.

The subject generator is adapted for wireless recharging of the generator's battery as well as the generators' ultrasonic power source. For this purpose, the generator is equipped with a receiver and a receiving antenna for wireless power transfer from an external power source and from an external ultrasonic energy generator.

The subject generator further includes a microprocessor which has an input for receiving readings from the electrically conductive electrodes and the echo electrodes, and which runs on the algorithm configured to determine presence of electromechanical dissociation based on electrical and mechanical signals from the heart to diagnose a life threatening heart rhythm.

The generator's electrodes transmit data to the microprocessor to confirm the presence of the non life-threatening heart rhythm based on electrical and mechanical signals from the heart to avoid generation of inappropriate pacing shocks.

In another aspect, the present invention is directed to a method for sensing and generating energy transmitted from and to the heart of a patient.

The subject method comprises the steps of:
forming a flexible elongated low-profile curvilinear generator,
attaching at least one parameter sensing electrode to the flexible generator,
embedding said flexible generator in a flexible shaft contoured to conform to the intercostal space of a patient, and
implanting the flexible generator embedded in said flexible shaft in the intercostal space of the patient with the at least one parameter sensing electrode in facing positional relationship with the heart of the patient.

The method further continues through the steps of:
operatively coupling a microprocessor to the generator (alternatively, the microprocessor can be embedded in the generator structure);
sensing parameters of the heart activity with the at least one parameter sensing electrode;
transmitting the sensed parameters to the microprocessor for processing thereat.

The microprocessor in the subject generator operates based on a routine which includes the steps of:
analyzing the sensed parameters;
producing a diagnosis of the cardiac situation;
forming a control signal based on the computed diagnosis of the cardiac situation; and
transmitting the control signal to the generator to produce a pacing signal if the sensed parameters are indicative of a life-threatening heart condition.

The subject method further continues through the steps of:
embedding piezoelectric crystals in the flexible generator, and
measuring the mechanical heart activity by the piezoelectric crystals; and
embedding electrically conductive electrodes in the flexible generator, and
measuring the electrical heart activity.

The piezoelectric crystals in the subject generator may be configured for serving as ultrasonic transducers forming
a Doppler sensor in the flexible generator for measuring the blood flow from the heart.

The subject method further comprises the steps of:
embedding a receiving antenna in the flexible generator,
positioning a power source external to the patient's body,
coupling a transmitting antenna to the power source, and
recharging the generator's battery by wirelessly transmitting electrical power from the external power source through the coupled transmitting and receiving antennas.

The subject method also comprises the steps of:
embedding a source of ultrasonic energy in the generator,
positioning an ultrasonic energy generator external to the patient's body,
wirelessly recharging the internal source of ultrasonic energy from the external ultrasonic energy generator, and
generating pacing ultrasonic pulses by the internal source of ultrasonic energy to be delivered therefrom to the heart subsequent to receiving the control signal from the generator's microprocessor.

These and other objects and advantages of the subject system and method will be apparent from reading the following Detailed Description of the Invention considered in conjunction with the accompanying Patent Drawings Figures.

BRIEF DESCRIPTION OF THE DRAWINGS

FIG. 2A is a schematic representation of the subject generator;

FIG. 2B is a cross-section of the subject generator taken along lines A-A of FIG. 2A;

FIG. 2C is a cross-section of the subject generator taken along lines B-B of FIG. 2A;

FIG. 2D is a prospective view of the subject generator with the electrodes facing the heart of a patient;

DETAILED DESCRIPTION OF THE PREFERRED EMBODIMENT(S)

Figure 1:
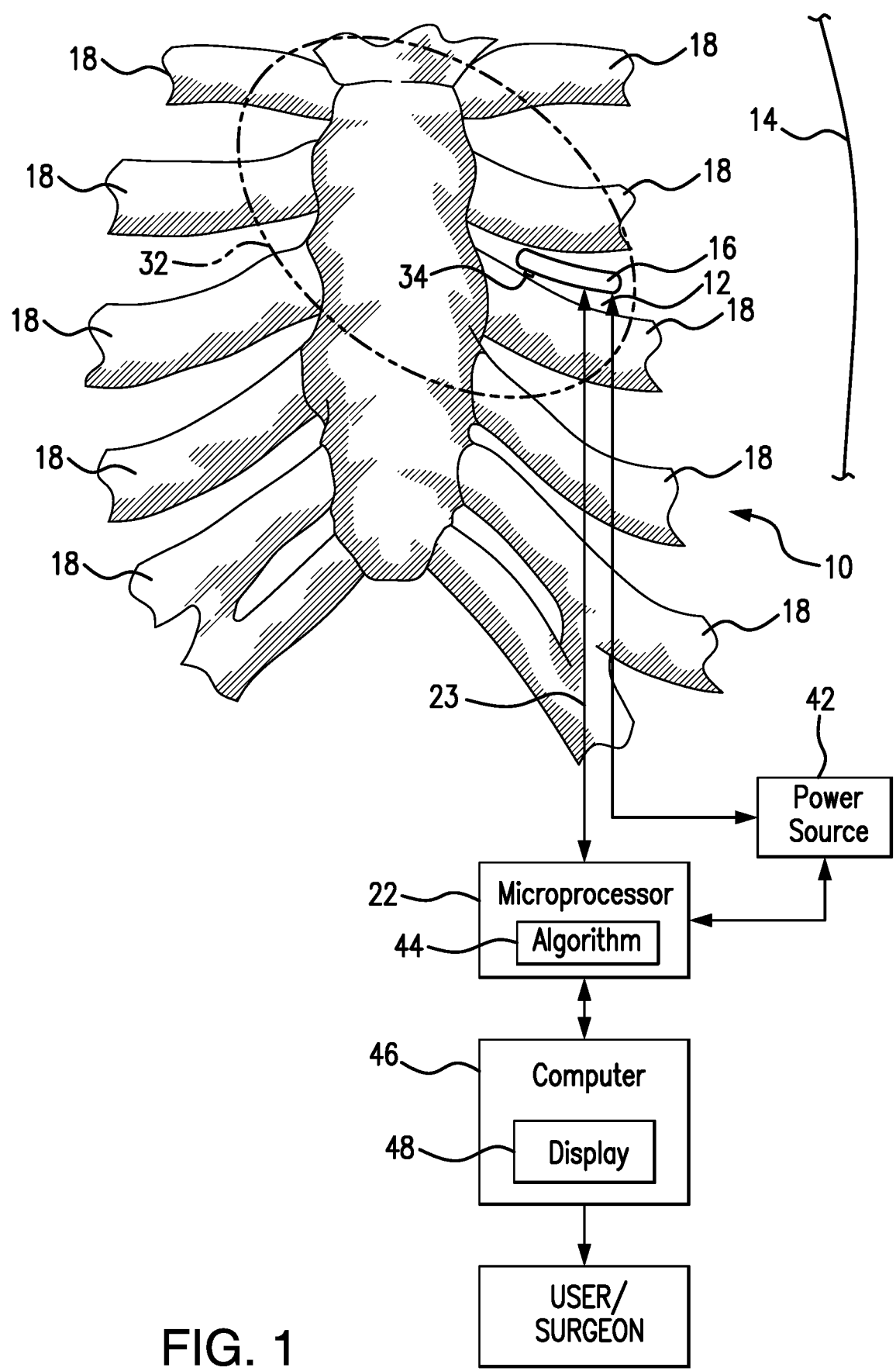
FIG. 1 is a schematic representation of the subject leadless pacemaker system configured for generating pacing pulses and sensing electrical and acoustic signals from a tissue within a patient's body depicting the subject electrical generator implanted along the intercostal space in the chest chamber of a patient.

Referring now to FIGS. 1-4, a pacemaker system 10 is designed for generating electrical, acoustic (ultrasound, Doppler), infrared, and magnetic energy directed to a mammalian tissue and sensing such energy from the tissue of interest. The intercostal space 12 of a patient's chest wall 14 is selected as an implantation site in order to avoid interference from bony structures, such as ribs. The intercostal space location, specifically, the fourth or fifth intercostal space, is positioned in close proximity to the heart of a patient without intervening lung tissue (that otherwise may interfere with electromagnetic or ultrasonic signals traveling to and from the heart).

The subject system 10 includes a pacemaker generator 16 adapted to be received within the body of a patient, and particularly, in the intercostal region 12 located between patient ribs 18. The generator 16 is formed as a flexible elongated low-profile (near-flat)member applicable to dynamically changing sites in the patient's body.

Figure 3:
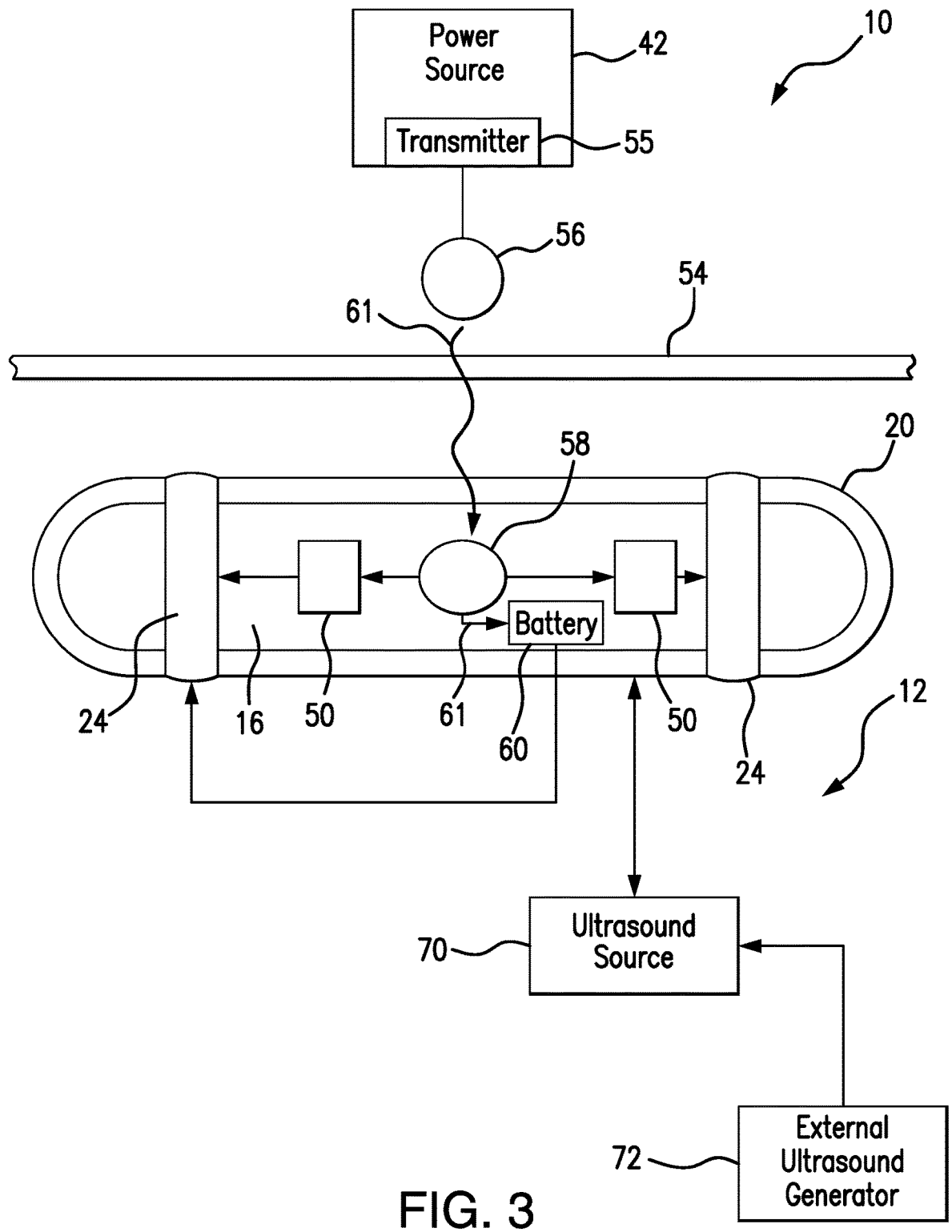
FIG. 3 is a schematic representation of the subject pacemaker system depicting antennas for recharging the subject generator via wireless power transfer.

The generator 16 is embedded within a tube-like shaft (also referred to herein as a generator's shield) 20, as shown in FIGS. 1-3. An important advantage of embedding the generator 16 within the shield 20 is that being embedded in the shield 20, the generator 16 is protected from an undesired interference with ultrasonic or electromagnetic signals traveling therearound.

The generator's shield 20 may be formed from conductive medical EMI/RFI plastic compound materials, polymeric materials with oriented nanotubes, electrically conductive elastomers, plastic substrate sprayed with a metallic ink, etc. A thin flexible layer of biocompatible conductive material capable of flexibly adapting to the contour and dimensions of the intercostal space, or any other dynamically changing space within the patient's body, is suitable for fabrication of the tube-like flexible miniature shield 20.

The generator's shield 20 and the generator 16 are both formed as flexible low-profile members contoured in a somewhat curvilinear shape along their length, and thus are suitable for insertion into the sites of the patient's body having a tortuous contour, such as, for example, the intercostal space.

The characteristics of the subject generator are presented in Table 1 in comparison to a prior art pacemaker.

The generator 16 has been fabricated which has a dimensional contour adaptable for insertion and containment within the shield 20. The generator 16 may, for example, have the following dimensions: about 7 cm$^3$ volume, about 7.0 cm or less in length, about 1.0 cm or less in width, and about 1.0 cm or less in height, in order to accommodate the intercostal space 12.

The electrically conductive shield 20 with the generator 16 embedded therein is preferably inserted within the intercostal space 12 in proximity to the heart chambers 32 within a patient's body.

The subject system 10 further includes a microprocessor 22, which may be an embedded microprocessor positioned in operative connection with the generator 16. Alternatively, the microprocessor 22 may be an external processor unit (for example, included in a computer 46) which is capable of a wireless communication with the generator 16 over a communication path 23 for wireless transmission of data corresponding to the heart activity thereto and command signals therefrom to the generator 16.

The generator 16 further is equipped with various double-action electrodes, one function of which is to operate as parameter sensing members. The double-action electrodes may include, for example, electrically conductive electrodes 24 and piezoelectric crystal sensors 26 disposed in a spaced apart relationship along the length of the generator 16 at predetermined positions.

In the system 10, the electrically conductive electrodes 24 are capable of sensing the electrical activity of the heart, as well as usable for delivering electrical stimulation pulses (signals) passing to and from the intercostal space 12 of the patient's chest 14 to a tissue of interest. Another type of electrodes used in the subject generator includes piezoelectric crystals 26 which are capable of sensing mechanical activity of the heart and the Doppler blood flow. The pacing energy may be also of an ultrasonic nature, which is delivered to the heart directly from the internal source of the ultrasonic energy 70 embedded with the generator 16 and implanted therewith in the intercostal region 12. Due to the close proximity of the generator 16 to the heart, the direct delivery of the pacing pulses in the leadless manner to the heart tissues is very efficient.

The electrically conductive electrodes 24 (also referred to herein as EKG or ECG electrodes) may be attached either to the generator 16 or to the generator's shield 20 and are positioned in a facing relationship with the heart 32 within the patient's chest 14. The electrodes 24 and component parts of the system 10 may be formed of suitable biocompatible conductive compositions, such as, for example, iridium, platinum, or like compositions, which provide optimal sensing, as well as pacing (or shock).

The electrodes 24 are embedded within the generator 16 or the shield 20 and are disposed in a contiguous contact with the patient's tissue of the intercostal space 12 for sensing electrical activity of the heart, as well as for low and/or high voltage pacing when commanded so by the microprocessor 22.

The present system 10 also uses a piezoelectric effect which is reversible so that materials or compositions may exhibit a direct piezoelectric phenomena (which is the internal generation of electric charge resulting from an applied mechanical force), or alternatively, a reverse piezoelectric phenomena (which is the internal generation of mechanical strain resulting from an electric field applied thereto), for example, from the electrical generator 16 enveloped by electrically conductive shield 20.

Piezoelectric sensing elements 26 (also referred to herein as ultrasonic sensing electrodes, or Doppler ultrasound transducers, or acoustic sensors, echo electrodes), may be formed of well-known compositions that include, for example, barium titanate and lead zirconate titanate which exhibit larger displacements when subjected to induced larger electric voltages than that found in natural monocrystalline materials.

In the subject system, the electrical generator 16 serves as an energy source (both electrical and ultrasonic) and, when implanted in the patient's body, is contained within a receiving space formed by the thin flexible wall of the tube-like electrically conductive shaft 20. The electrically conductive shaft 20 is implanted within the mammalian body within the intercostal space and is secured in place by an appropriate anchoring mechanism 34, such as, for example, surgical sutures to obtain an adequate echocardiographic window of the pumping heart chambers, as well as electrical signals.

In this manner, the system 10 both generates and senses electrical and ultrasonic energy directed to and from the patient's heart tissue, respectively.

As shown in FIGS. 2A-2D, the electrodes 24 and piezoelectric sensing elements 26 are displaced one from the other by a predetermined distance along the length of the generator/shaft.

Specifically, in the preferred embodiment, the subject generator 16 is equipped with a first EKG (or ECG) electrode 24 and Doppler ultrasound transducers electrodes 26 which are interposed between the EKG (or ECG) electrodes 24. Each electrode component is selectively spaced at a distance in the centimeter range center-to-center from each other around the cross-contour of the generator 16 or the shaft 20.

The electrodes 24, 26 are coupled wirelessly or by wires via an interconnector (not shown) with the microprocessor 22. The microprocessor 22 processes the EKG signals (from the electrodes 24) and the Doppler signals (from the piezoelectric crystal sensors 26) to obtain various parametric information on the electrical and mechanical activity of the heart, as well as the blood flow for making a precise diagnosis of the tissue being examined.

The shaft 20 is a somewhat tubular member having an oval contoured hollow interior to conduct heart sounds to the sensors 26. Thus shaped, the generator's shaft 20 constitutes a near-flat, low-profile, curved member adapted for implantation in the intercostal space in the chest chamber. The generator's shield 20 is a thin walled flexible structure, having an internal diameter of any suitable size for embedding therein the flexible generators with the electrodes, the generator's battery 60, the internal ultrasonic source 70, and conductive paths or leads through it to the microprocessor 22.

In a preferred embodiment, oval shaped EKG electrodes 24 and ultrasound sensing electrodes 26 are circumferentially positioned around the cross-sectional periphery of the generator 16 or the shaft 20 at respective longitudinally spaced locations. Equal spacing between respective ones of the EKG electrodes 24 and Doppler ultrasonic transducers 26 is provided. It is also important that the distance between the electrodes is within centimeters range center-to-center to provide an optimum organ stimulating mechanism combined with localization of the echo data produced by the Doppler ultrasonic transducer resulting in improved echocardiographic data and imaging.

The EKG electrodes 24 are oval rings which may be formed of electrically conductive medically inert material, such as, for example, stainless steel, silver, or metallic paint. The diameter of these oval rings, in their cross-section, has a large and small orthogonal dimensions, which conform to a somewhat low profile, near-flat contour of the generator 16 and the generator's shaft 20.

The contour of the electrodes 24 substantially conforms to the cross-sectional contour of the generator 16 or the shaft 20, so that the oval rings may be snuggly slipped onto the exterior of the generator 16 or the shaft 20 but will tightly bind to the exterior of the shaft 20 so as to remain in position. It should also be understood that the electrodes may be fixed in location by other means, such as welding, soldering, adhered with conductive epoxy or by placement in a formed channel.

The Doppler ultrasonic transducers 26 are formed as oval rings of piezoelectrical material having metallic conducting layers formed on their inner and outer surfaces. The oval ring 26 is contoured to snuggly fit around the circumference of the generator 16 or the shaft 20.

The Doppler ultrasonic transducers 26 are coupled with a circuit which applies a high frequency electrical signal to a transmitting transducer to cause the transmission of ultrasonic energy in a fairly broad beam. Electrical output signals from the receiving transducer, resulting from the return signals of the transmitted ultrasonic energy from objects within the beam are compared with the high frequency electrical signal applied to the transmitting transducer to develop a Doppler signal representative of any frequency shift caused by the relative movement between an object and the probe. The Doppler signal is then amplified and converted to a monitor system which comprises a Doppler signal processor.

In a preferred embodiment of the subject system, the Doppler ultrasonic transducers 26 are used both for the transmission and reception of ultrasonic energy in order to meet the size constraints imposed upon the intercostal space in order to simplify the cardiac event detecting process.

In a preferred embodiment, Doppler ultrasonic transducers 26 transmit acoustic energy at ultrasonic frequencies, pause for a predetermined period (ultrasonic window) and then receive signals echoed from the target zone (for example, the heart tissue). The pulsed Doppler mode is preferred over a continuous wave Doppler mode, particularly in a highly compact system designed for inserting into the body because the pulsed mode allows for a higher-frequency transducer requiring an inherently smaller crystal for generating the ultrasonic beam.

Further, in the pulsed Doppler mode, a single crystal acts sequentially, as both the transmitter and receiver avoiding the necessity of a second transducer and thereby reducing the size requirement of the subject generator. Likewise, the pulsed Doppler mode requires less energy than the continuous wave Doppler mode. Such a reduction in energy requirements is highly desirable since it avoids undesirable cardiac reactions.

Interconnections between the electrodes 24, 26 and the microprocessor (and other pacing equipment) may be provided via several mechanisms. For example, longitudinal conductive pathways, or leads (not shown) may be embedded in a recess in the wall of the shaft 20, on the exterior or interior surface of the generator's shaft 20, or in the lumen of the shaft 20. Conductive pathways may be of identical cross-sectional area and may be selected from wire conductors, coaxial cable, and optical fibers. Any flexible electrically conductive materials which are biocompatible may be used for this purpose.

Alternatively, interconnections between the electrodes 24, 26 and the microprocessor 22 may be via a wireless communication channels. The wireless communication will require transceivers, and (or transmitting and receiving) antennas as a means of communicating signals.

The generator 16 is long enough to permit positioning of the EKG electrodes 24, and ultrasonic transducers 26 in the intercostal space closely adjacent to the heart of the patient. Healthy hearts make four characteristic sounds referred to as the first, second, third, and fourth cardiac sounds. The first and second sounds are the principle sounds. The first is deeper and longer and is caused by the contraction of the ventricles and the closure of the valves between the atria and the ventricles. The second sound is shorter and is caused by the closure of the valves between the ventricles and the two large arteries, i.e., the aorta and the pulmonary artery by which the blood leaves the ventricles. The third and fourth sounds are less audible. The sound is caused by the flow of blood into the ventricles. The fourth sound is caused by the contraction of the atria. By monitoring these cardiac impulses, the generator can be implanted in the intercostal space in the desired position relative to the specific heart chamber.

A normal electrocardiograph exhibits complexes which have been labeled as the P, QRS, and T complexes of signals. The P wave corresponds to the depolarization of the atria. The QRS is the repolarization of the atrium and the depolarization of the ventricles. When the same signals are monitored by a probe in the esophagus, the P wave is much greater relative to the QRS complex, which is indicative of placement near the atrium. Therefore, by connecting the generator 16 to specific equipment it is possible to place the generator 16 at the position with the maximum measured P wave signal.

The longitudinal spacing between the ultrasonic transducers 26 and the EKG electrodes 24 are critical for providing improved accuracy of monitoring heart parameters with optimum echocardiographic results. The EKG electrodes 24 should be within centimeters center-to-center of the ultrasonic transducers 26. This assures that adequate contact of the echo producing mechanism will also provide adequate contact of the EKG electrode means at essentially the same location in the body.

The system 10 may be surgically implanted within the patient's body. In certain exemplary applications, the shield 20 may be introduced percutaneously over an adaptor under the fluoroscopic or ultrasound guidance into the intercostal space 12 and positioned with the EKG electrodes 24 and the piezoelectric crystals 26 facing the desired heart chambers for sensing mechanical and electrical heart activities, respectively.

The current invention advantageously provides positioning of the electrodes 24 and piezoelectric elements 26 in close proximity to the heart 32 without intervening skin, ribs or lung tissue. The system 10 may include an anchoring mechanism 34 for securing the shield 20 in a stable position within the intercostal space 12. In accordance with one embodiment of the present invention, the wireless piezoelectric elements 26 for ultrasonic sensing and pacing are implanted within the subcutaneous tissues of the intercostal space 12.

For the positioning of the generator implant 16, the patient's at-rest heart rate is measured and recorded. Continuous monitoring of the vital signs, transcutaneous oximetry and surface EKG is conducted. The generator 16 within the shaft 20 is then inserted into the intercostal space 12 and positioned where the atria of the heart may be visualized on an echocardiography display screen 48 (shown in FIGS. 1 and 4). The echographic images are generated with existing technology, using piezoelectric crystals and a phased array echocardiographic probe that transmits suitable frequencies. Return signals generated by the ultrasonic transducer as a result of the reflected ultrasounds are transmitted by existing fiber optic technology to an echocardiographic machine such as the Hewlett-Packard, Series 1000 manufactured by Hewlett-Packard Corporation, sold under the Trademark SONOS 2000 which converts the frequency data to an image display on the echocardiographic screen. Concurrently, the images may be recorded on video tape.

As the generator 16 approaches the atrium of the heart, a distinct EKG signal is displayed on the echocardiographic screen. The EKG signal shows a prominent P wave (an atrial activation wave form). As the generator is advanced further along the length of the intercostal space, the EKG signal visualizes a prominent R wave (ventricular activation wave form) on the echocardiographic screen. As the generator 16 is further displayed, and although the echocardiographic signal may show little change, subtle movement of the generator 16 may result in significant changes in the P-QRS-T morphology of the EKG signal obtained from the generator 16. The EKG signal is obtained from the contact of the EKG electrode 24 with the heart which transmits the electrical impulses emanating from the heart through the EKG electrode 24 to the echocardiographic machine and the EKG signal is displayed simultaneously on the video screen. Since more than one EKG electrode 24 is utilized in the subject system, more than one signal may be simultaneously displayed on the video screen. Thus, EKG and ultrasonic signals are generated from the same location to provide a much improved and more accurate echocardiographic image.

In another embodiment, the subject generator can be used to pace the heart to desired stress levels. At the onset of stress, emotion, exercise, or even in anticipation of these conditions in a person with a normal heart, the sympathetic nervous system responds by constricting the interiors of central visceral and peripheral veins, increasing cardiac contractility and elevating heart rate. In some cases, the heart does not have the ability to raise the heart rate to allow for accurate diagnosis of coronary disease. The subject generator 16, through the EKG electrode components 24, may be positioned more precisely and proximate in relation to the specific chamber of the heart to provide an electrical pulse having a lower strength than normally required.

The close proximity to the heart chamber and the critical distance of the ultrasonic transducers 26 from the EKG pacing electrodes 24 requires less electrical energy and produces an improved echocardiographic image 26, since the ultrasonic transducers which receive the sonic output (atrial or ventricular wall motion of the stressed heart) may be positioned more accurately in relationship to a particular chamber.

It has been found that the shorter the distance between the echo elements 26 and EKG elements 24, the more accurate is the correlation between the echo and EKG display, the better is the EKG location of the echo image, the less need for maneuvering the echo/EKG generator to obtain simultaneous echo and EKG signals from the same location within the body or body surface in the case of transthoracic or other surface echocardiogram. The distance in the range of centimeters between echo and EKG components is therefore important since significant changes in signals may result in small changes of position of the probe in the esophagus.

The system 10 is adaptable for incorporating high voltage pacing electrodes 24 as well as low voltage pacing electrodes 24.

In an alternative embodiment, shown in FIG. 3, the generator 16 may contain receivers 50 and a coupling antenna 58 to enable wireless recharging of the battery 60 within the generator 16 from an external power source 42 which, for the purposes of wireless recharging of the generator's battery 60, is provided with a transmitter unit 55 for transmitting the energy via the transmitting antenna 56 through the skin layer 54.

The receivers 50, subsequent to receiving the energy 61 by the receiving antenna 58, directs the energy to the battery 60 and/or the electrodes 24, 26 to support operation of the generator 16.

Electromagnetic energy transfer used in the subject system is the transmission of electric field energy from the wireless transmitter 55 (connected to the power source 42) to a distant receiver 50 where it is converted back to an electric current. Specifically, induction coils 56 may be used in the wireless transmitter 55 to create a high frequency alternating electromagnetic (EM) field that is transmitted to a coil 58 installed in the receiver 50.

The receiver coil 58 may be fabricated of silver plated copper or ultrathin lightweight aluminum and is housed within the generator 16 of the pacemaker where the EM field is converted to electric current in order to charge the device's battery 60.

Referring to FIGS. 2A and 3, the subject generator 16 also is designed for wireless transmission of the ultrasonic power from the external ultrasonic generator 72 (which is positioned external to the patient's body) to the internal ultrasonic source 70 implanted in the patient body along with the generator 16 in the intercostal space 12. The ultrasonic energy is used in the subject system for operation of the piezoelectric crystals 26 and for direct delivery of the ultrasonic pulses to the heart when needed under command of the microprocessor 22.

The subject system contemplates delivering to the heart the pacing pulses of other types, for example, magnetic, in addition to the electrical and ultrasonic pacing.

The intercostal space 12 in close proximity to the heart 32 is an ideal location for the generator 16. Being located in the intercostal space 12, the generator 16 would normally be free of intervening bone matter or lung tissue that might otherwise interfere with ultrasonic and electrical signals, which tend to transmit poorly through air present in lung tissue, and through the bone matter. The generator 16 may be flexible, curved, or made of displaceable pacing and imaging elements so as to conform (in the contour and dimensions) to the spaces between the ribs, and minimize unwanted cosmetic chest asymmetry.

The generator 16 is surgically implanted within the intercostal space 12 at an optimum location determined by the ultrasonic (or echocardiographic) window (as presented in previous paragraphs). The imaging elements (electrodes 24 and piezo-electric crystals 26) are disposed to face the heart 32 or the tissue to be stimulated, such as the right ventricular outflow, left ventricle or atrial appendage.

The piezoelectric crystal electrodes 26 (also referred to as echocardiographic electrodes, or Doppler ultrasound transducer electrodes) may face the heart 32 or the ribs 18, or may even face away from the heart, depending on the level of intercostal muscle interference with the heart's electrical signals.

Preferably, an external power source 42, shown in FIG. 3, is positioned behind (or beside) the pacing (or imaging) elements (24, 26), so as not to interfere with their function. The power source 42 may be of any suitable type commercially available, such as, for example, electrochemical or electromechanical power source.

According to one aspect of the present invention, a convenient and effective method of securely implanting a pacemaker lead into the intercostal space is provided.

The locations are determined by the resultant pacing induced electrical and mechanical efficiency. The electrodes are fabricated of suitable material such as platinum, iridium that provides optimal sensing, pacing, and shock.

In certain other embodiments, the generator that energizes the leads is powered by a battery, and produces electrical stimulation.

In certain other embodiments, the generator that energizes the leads is powered by a stimulator that produces electrical current via body tissue without the need for a wire lead.

In certain other embodiments, the generator produces ultrasound energy that is transmitted directly to the cardiac conduction tissue to cause pacing without the need for secondary piezoelectric crystals embedded within the heart.

In certain other embodiments, the generator has a curved contour and is elongated in shape in order to conform to the intercostal space (the space between the ribs of the chest overlying the heart), and permit close proximity to cardiac structures for optimal transfer of electrical, ultrasound, Doppler, infrared and magnetic signals therewith.

The generator is operable to detect cardiac electrical activity without the use of intra-cardiac electrodes.

In certain other embodiments, the generator is operable to emulate a 12-lead electrocardiogram by detecting cardiac electrical activity from various locations of the heart as detected from the intercostal space.

In certain other embodiments, the generator is operable to induce cardiac electrical signals without the use of wires.

In certain other embodiments, the generator is operable to detect cardiac mechanical activity by way of ultrasound or Doppler signals without the use of intra-cardiac piezoelectric crystals.

In certain other embodiments, the generator is operable to induce cardiac mechanical contraction by way of ultrasound signals without the use of wire electrodes.

In certain other embodiments, the generator is operable to receive cardiac electrical and mechanical action and synchronize the output signals to electrodes implanted in various cardiac chambers in order to provide optimal cardiac contraction and function.

Figure 4:
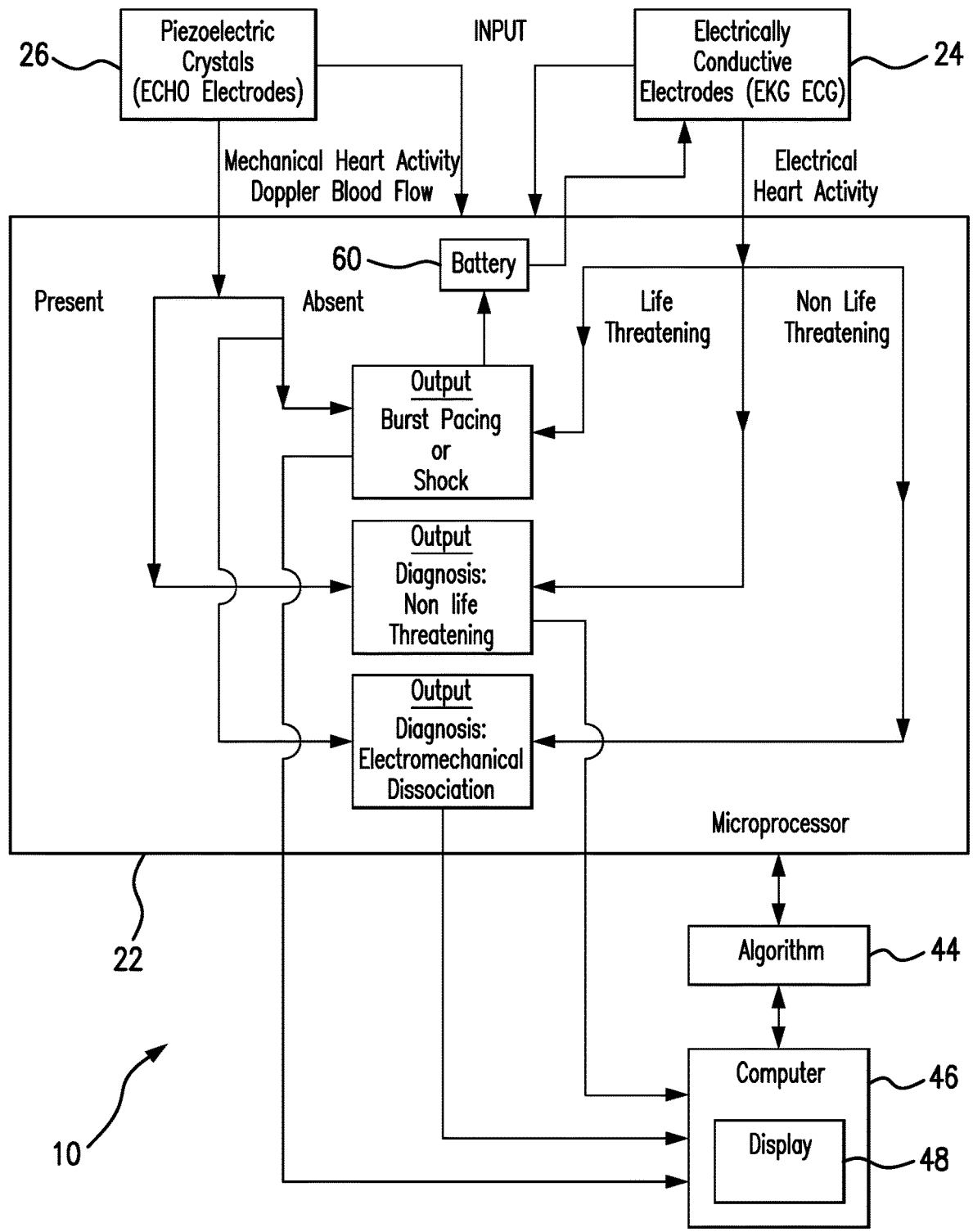
FIG. 4 is a schematic representation of an embodiment of the subject pacemaker system equipped with the generator's microprocessor operating to continuously receive input from the EKG electrodes and the piezoelectric sensors regarding electrical and mechanical/Doppler flow activities of the heart, producing a diagnosis of the cardiac situation, and responding by issuing control signals to "Pace", "Burst Pacing", or "Shock" for delivery of pacing to the heart chambers if a life-threatening cardiac situation has been detected, or to "Observe" for the non life-threatening cardiac situation.

Referring to FIG. 4, depicting schematically the operation of the microprocessor 22 for analysis of the cardiac situation and pacing/shock, when needed, the algorithm 44 underlies the operation of the system 10 and may run either on the microprocessor 22 embedded in or positioned in proximity to the generator implant 16 in the patient's body, or on the external computer 46. The computer 46 may be operatively coupled to the microprocessor 22 for operating the current system 10.

As shown, the readings from the piezoelectric sensor 26, responding to the mechanical heart activity, as well as the readings from the EKG electrodes 24, corresponding to the electrical heart activity, as well as the readings from the electrodes 26 corresponding to the Doppler blood flow, are input, wirelessly or through a wired connection, into the microprocessor 22.

When the microprocessor 22 determines that the mechanical heart activity and the Doppler blood flow are present, the microprocessor makes a decision of the non-life threatening diagnosis. If however, the mechanical heart activity and Doppler's blood flow readings are absent, the microprocessor 22 commands the generator 16 to generate a pulse, also known as "burst pacing" or "shock" to be administered to the heart.

Further, if the electrical heart activity signal produced by the EKG electrodes 24 shows a life-threatening condition, the microprocessor commands the generator to produce a "burst pacing" or "shock" pulse to be administered to the heart.

If, however, the readings of the electrodes 24 for the electrical heart activity are non life-threatening, the microprocessor produces a diagnosis of electromechanical disassociation.

Responsive to the diagnosis of non life-threatening condition produced by the microprocessor 22, the causes using activation of the electrodes and sensors are searched and treated. These causes may include supraventricular tachycardia, QRS and T wave double-sensing, electromagnetic interference, diaphragmatic sensing, lead fracture, insulation break, or lead dislodgement.

When the microprocessor 22 produces the diagnosis of electromechanical disassociation, the search and treatment of causes is performed. These causes may include hypovolemia, hypoxia, acidosis, hyperkalemia or hypoglycemia, hypothermia, drug overdose, cardiac tamponade, or tension pneumothorax.

For the convenience of a user/cardiologist, all information may be displayed on a display 48 which may be presented either to the patient or to a cardiologist located remotely from the patient.

The microprocessor 22 may be located remotely from the pacemaker system 10 or may be a portion of the pacemaker system 10. The communication between the microprocessor and the electrodes (both EKG electrodes 24 and echo electrodes 26) may be wireless or through the wired transmission. The communication between the microprocessor 22 and the computer 46 may be through the wireless communication or through wired signal transmission.

In the presence of ventricular fibrillation or flutter and very rapid ventricular tachycardia, the ventricles will demonstrate no motion and cease to function as a pump. Also, in this situation, there is an absence of blood flow detected by Doppler signals. On the other hand, if life-threatening arrhythmia is detected by the electrodes, but mechanical function and blood flow are preserved, then the arrhythmia is not life threatening and the electrical signal is associated with adequate heart function and blood flow.

Alternatively, the microprocessor may also trigger the embedded electrodes to deliver pacing or shocking electric impulses in the event of an ultrasonic signal corresponding to the situation when the heart stopped pumping and that there is an absence of blood flow. In this situation, the receipt of the ultrasonic signal corresponds to confirming of a life threatening heart rhythm that requires immediate electrical pacing or shock which requires the microprocessor to trigger the embedded electrodes to deliver the pacing or shock pulses to the heart of the patient.

The present description with reference made to the accompanying Drawing Figures is not to be interpreted in a limited sense. It is to be noted that the principles of the subject invention are also applicable to alternative embodiments and may be utilized without departing from the scope of the current invention, as defined in the Claims appended to this description.

What is claimed is:

1. A system implantable in the intercostal space in a patient body in closed proximity to and facing position relative to the heart of a patient for generating and sensing electrical and ultrasonic energy transmitted to and from a tissue of interest within a patient body, comprising:
   a flexible tube-like shield member having an elongated low-profile curvilinear contour and adapted to conform with an arcuated contour of an intercostal space envelope of a patient's body for being implanted in the intercostal space between a pair of adjacent ribs in substantial congruence with the intercostal space contour, said flexible shield member having thin walls defining an elongated receiving space therebetween;
   a flexible generator received within said receiving space in said flexible shield member and adapted for producing stimulation energy and for sensing electrical and ultrasonic energy associated with a tissue of interest; and
   a plurality of double-action electrodes operatively coupled with and embedded within said flexible generator, said plurality of double-action electrodes being configured to perform a double function, including (1) sensing of the electrical and mechanical heart activity of the heart of a patient and blood flow parameters, and (2) generating therapeutic stimulation pulses directed to the heart in response to a cardiac situation detected in correspondence to the heart activity and the blood flow parameters sensed by said double-action electrodes.

2. The system as recited in claim 1, wherein said plurality of double-action electrodes includes at least one piezoelectric crystal embedded within said shield member, said at least one piezoelectric crystal being configured to perform measurements of heart function by continuous and pulsed echocardiographic signals for diagnostic purposes, and to deliver high energy ultrasonic bursts for therapeutic of the heart tissue.

3. The system as recited in claim 1, wherein said flexible shield member is configured for insertion within a patient's intercostal space percutaneously or surgically.

4. The system as recited in claim 1, wherein said plurality of double-action electrodes include at least one electrically conductive electrode selected from the group consisting of high voltage pacing electrodes and low voltage pacing electrodes.

5. The system as recited in claim 4, wherein said generator embedded within said flexible shield is configured to detect electrical activity of the patient's heart based on the readings of said at least one electrically conductive electrode.

6. The system as recited in claim 2, wherein said generator embedded within said flexible shield is configured to detect mechanical activity of the patient's heart based on the reading of said at least one piezoelectric crystal.

7. The system as recited in claim 4, wherein said generator embedded within said flexible shield is configured to generate electrical energy directed through said high voltage pacing electrodes or said low voltage pacing electrodes to the patient's heart.

8. The system as recited in claim 2, wherein said generator includes an internal ultrasonic energy source operatively coupled to and implanted in the patient's body along with said generator and said at least one piezoelectric crystal, wherein said at least one piezoelectric crystal, being powered by said internal ultrasonic energy source, produces pulsed and continuous ultrasound signals to detect mechanical heart function or the lack thereof.

9. The system as recited in claim 8, wherein said plurality of double-action electrodes includes an echo electrode, and wherein said internal ultrasonic energy source in said generator includes an ultrasound Doppler source positioned in proximity to and in operative coupling with said echo electrode for pacing.

10. The system as recited in claim 9, wherein said generator embedded within said flexible shield is configured to produce electric shock pulse responsive to combined acquired readings on the electrical and mechanical activity of the patient's heart when a life threatening heart rhythm has been diagnosed.

11. The system as recited in claim 1, further including an external power source and a transmitting antenna operatively coupled to said external power source,
    wherein said generator embedded within said flexible shield includes a receiver and a receiving antenna operatively coupled to said receiver for wireless power transfer between said external power source and a battery in said generator.

12. The system as recited in claim 1, further including an external ultrasonic generator and a transmitting antenna operatively coupled to said external ultrasonic generator,
    wherein said generator embedded within said flexible shield includes an internal ultrasonic source, a receiver and a receiving antenna operatively coupled to said receiver for wireless power transfer between said external ultrasonic generator and said internal ultrasonic source implanted along with said generator in the patient's body.

13. The system as recited in claim 10, further including a microprocessor operatively coupled to said generator, wherein said plurality of double-action electrodes transmit data to the microprocessor to determine presence of electromechanical dissociation based on electrical and mechanical signals from the heart or to diagnose a life-threatening heart rhythm, or to confirm the presence of the non life-threatening heart rhythm based on electrical and mechanical signals from the heart to avoid inappropriate shocks.

14. The system as recited in claim 1, wherein said flexible shield is formed of a biocompatible electrically-conductive composition.

15. The system as recited in claim 1, wherein said flexible shield is contoured to assume a contour of the intercostal space.

16. A method for sensing energy transmitted from and generating energy transmitted to the heart of a patient, comprising the steps of:
    forming a flexible generator,
    embedding said flexible generator in a flexible tube-like shield having an elongated low-profile curvilinear contour and adapted to conform to an arcuated contour of an intercostal space envelope of a patient, and
    attaching at least one double-action electrode to said flexible generator embedded in said flexible shield, said at least one double-action electrode being configured to sense at least one parameter associated in the heart activity and to produce a pacing signal responsive to said sensed at least one parameter;
    implanting said flexible generator embedded in said flexible shield in the intercostal space of the patient between a pair of adjacent ribs in substantial congruence with the intercostal space contour with said at least one parameter sensing electrode in proximity to and in facing positional relationship with the heart of the patient;
    operatively coupling a microprocessor to said flexible generator;
    sensing said at least one parameter of the heart activity with said at least one parameter sensing electrode;
    transmitting said sensed at least one parameter to said microprocessor for processing thereat; and
    generating, at said microprocessor, a control signal responsive to said sensed at least one parameter and transmitting said control signal to said flexible generator to produce a pacing signal if said sensed at least one parameter is indicative of a life-threatening heart condition.

17. The method of claim 16, further comprising:
    embedding piezoelectric crystals in said flexible generator, and
    measuring the mechanical heart activity by said piezoelectric crystals.

18. The method of claim 16, further comprising:
    embedding electrically conductive electrodes in said flexible generator, and
    measuring the electrical heart activity.

19. The method of claim 16, further comprising:
    embedding a Doppler sensor in said flexible generator, and
    measuring blood flow of the heart.

20. The method of claim 16, further comprising:
    embedding a receiving antenna in said flexible generator,
    embedding a battery with said flexible generator,
    embedding an internal ultrasonic energy source with said flexible generator,
    positioning a source of energy external to the patient's body, wherein said external source of energy includes a source selected from a group including an electrical power source and ultrasonic power source,
    coupling a transmitting antenna to said external source of energy, and
    wirelessly transmitting energy from said external source of energy through said transmitting and receiving antennas to said battery and said internal ultrasonic energy source, respectively, embedded in said generator.

* * * * *